(12) United States Patent
Morris et al.

(10) Patent No.: US 10,617,985 B2
(45) Date of Patent: Apr. 14, 2020

(54) GAS SENSOR MODULE WITH FIELD REPLACEABLE, INGRESS PROTECTED, SENSOR FILTER

(71) Applicant: Rosemount Inc., Shakopee, MN (US)

(72) Inventors: Mark B. Morris, Cokato, MN (US); Greg E. Gindele, Maple Lake, MN (US); Hun Chhuoy, Savage, MN (US)

(73) Assignee: Rosemount Inc., Shakopee, MN (US)

( * ) Notice: Subject to any disclaimer, the term of this patent is extended or adjusted under 35 U.S.C. 154(b) by 23 days.

(21) Appl. No.: 15/449,359

(22) Filed: Mar. 3, 2017

(65) Prior Publication Data

US 2018/0085696 A1 Mar. 29, 2018

Related U.S. Application Data

(60) Provisional application No. 62/401,440, filed on Sep. 29, 2016.

(51) Int. Cl.
*B01D 46/00* (2006.01)
*G01N 33/00* (2006.01)

(52) U.S. Cl.
CPC ..... *B01D 46/0005* (2013.01); *G01N 33/0027* (2013.01); *B01D 2265/028* (2013.01); *B01D 2271/02* (2013.01)

(58) Field of Classification Search
CPC .... G01N 1/24; G01N 33/009; G01N 33/0011; G01N 1/2273; G01N 7/10; G01N 1/405; G01N 21/783; G01N 27/126; G01N 2030/025; G01N 7/04; G01N 27/12; G01N 1/2214; G01N 33/0027; B01D 2253/102; B01D 53/04; B01D 53/0462; B01D 53/02;
(Continued)

(56) References Cited

U.S. PATENT DOCUMENTS 5,363,690 A * 11/1994 Evangelista ....... G01N 33/0006
73/31.02
5,879,527 A * 3/1999 Kiesele .............. B01D 39/1661
204/276
(Continued)

FOREIGN PATENT DOCUMENTS

EP PCT/EP2002/000369 A2 7/2002
RU 2082956 C1 6/1997
WO 2016-030735 A1 3/2016

OTHER PUBLICATIONS

Detcon Hydrogen Sulfide Sensor Model DM-700-H2S Product Data Sheet, retrieved from http://www.detcon.com/1-documents/data_sheets/1-sensors/Model%20700/DM-700/Hydrogen%20Sulfide%20DM-700-H2S%20PDS.pdf, retrieved on Aug. 22, 2017, 2 pages.
(Continued)

*Primary Examiner* — John Fitzgerald
*Assistant Examiner* — Truong D Phan
(74) *Attorney, Agent, or Firm* — Christopher R. Christenson; Kelly, Holt & Christenson PLLC (57) ABSTRACT

A gas detection device includes a gas sensor module, configured to detect a gas, and a filter assembly. The gas sensor module includes a gas sensor disposed within a gas sensor housing and circuitry coupled to the gas sensor housing. The circuitry is configured to provide an indication of the gas. The filter assembly is configured to couple to the gas sensor housing and protect the gas sensor from particulates.

11 Claims, 6 Drawing Sheets

(58) Field of Classification Search
CPC ............ B01D 53/0454; B01D 53/0438; B01D 2259/40096; B01D 2259/40088; B01D 2265/028; B01D 2271/02; B01D 46/0005
USPC .... 73/23.2, 31.01, 31.02, 31.07; 422/83, 88; 95/148; 96/17, 18, 108–154
See application file for complete search history.

(56) References Cited

U.S. PATENT DOCUMENTS

| | | |
|---|---|---|
| 6,252,510 B1 | 6/2001 | Dungan |
| 6,670,887 B2 | 12/2003 | Dungan |
| 6,794,991 B2 | 9/2004 | Dungan |
| 7,089,778 B2 | 8/2006 | Rabenecker et al. |
| 7,345,590 B2 | 3/2008 | Nakano et al. |
| 8,358,105 B2 | 1/2013 | Barten et al. |
| 2008/0274401 A1* | 11/2008 | Broy ................. H01M 4/38 429/163 |
| 2011/0042570 A1* | 2/2011 | Wong ................. G01N 21/3504 250/340 |
| 2012/0297860 A1* | 11/2012 | Izawa ................. G01N 27/124 73/31.05 |
| 2012/0313370 A1* | 12/2012 | Pompeii ............. B01D 46/0024 285/400 |
| 2013/0062223 A1* | 3/2013 | Rabbett ............. G01N 27/4074 205/793 |
| 2013/0327005 A1* | 12/2013 | Menssen ............ B01D 46/2411 55/493 |
| 2014/0083852 A1* | 3/2014 | Yamamoto ......... G01N 27/4072 204/415 |
| 2014/0263099 A1* | 9/2014 | Patera ................. B01D 35/147 210/767 |
| 2014/0295690 A1* | 10/2014 | Quero pacheco .... H01R 13/562 439/271 |
| 2014/0326081 A1* | 11/2014 | Pierry ................. G01N 1/2205 73/863.23 |
| 2015/0177206 A1 | 6/2015 | Basham et al. |
| 2015/0204830 A1 | 7/2015 | Arunachalam |
| 2015/0265860 A1* | 9/2015 | Kennedy ............. F16B 45/02 182/3 |
| 2016/0084729 A1* | 3/2016 | Huseynov ............ G01M 3/24 73/40.5 A |
| 2016/0213954 A1* | 7/2016 | Ding ................... B01D 46/0086 |
| 2017/0217634 A1* | 8/2017 | Hendrickson ...... B65D 21/0204 |
| 2017/0276634 A1* | 9/2017 | Saffell ................ G01N 27/40 |
| 2018/0015505 A1* | 1/2018 | Stevenson ............ B06B 1/0644 |

OTHER PUBLICATIONS

Det-Tronics Electrochemical Toxic Gas Detector GT3000 Series Specification Data, retrieved from http://www.det-tronics.com/ProductCatalog/GasDetection/Documents/90-1199-10.1-GT3000.pdf, retrieved on Aug. 22, 2017, 2 pages.

International Search Report and Written Opinion for International Patent Application No. PCT/US2017/051443, dated Dec. 22, 2017, 14 pages.

First Examination Report for Australian Patent Application No. 2017334471 dated Sep. 3, 2019, 3 pages.

Office Action and Search Report for Russian Patent Application No. 2019112452 dated Oct. 14, 2019, 12 pages with English Translation.

Russian Office Action dated Jan. 20, 2020 for Russian patent application No. 2419112452, 7 pages including English translation.

* cited by examiner

GAS SENSOR MODULE WITH FIELD REPLACEABLE, INGRESS PROTECTED, SENSOR FILTER

CROSS-REFERENCE TO RELATED APPLICATION

The present application is based on and claims the benefit of U.S. Provisional Patent Application Ser. No. 62/401,440, filed Sep. 29, 2016, the content of which is hereby incorporated by reference in its entirety.

BACKGROUND

The process industry often employs gas sensors in order to detect the presence of a particular gas, often as part of a safety system. This is important as many gases may be harmful to human health and/or the environment. Industrial gas sensors are normally mounted near the process area of a plant or control room, or an area to be protected. Generally, industrial gas sensors are installed at fixed locations and to communicate with monitoring systems.

SUMMARY

A gas detection device includes a gas sensor module, configured to detect a gas, and a filter assembly. The gas sensor module includes a gas sensor disposed within a gas sensor housing and circuitry coupled to the gas sensor housing. The circuitry is configured to provide an indication of the gas. The filter assembly is configured to couple to the gas sensor housing and protect the gas sensor from particulates.

DETAILED DESCRIPTION OF ILLUSTRATIVE EMBODIMENTS

Gas sensors may be used to detect combustible, flammable and toxic gases. Gas sensors may include infrared point sensors, ultrasonic sensors, electrochemical gas sensors, and semiconductor sensors. To work properly, gas sensors must not become compromised by moisture, dust, or other types of debris. If compromised, gas sensors may not be able to accurately sense gases, and, over time, may even become damaged leading to their eventual replacement.

Often, gas sensors are protected using a barrier to shield out unwanted particulates. However, to install the barrier, a known protocol is often followed requiring a number of different tools. Additionally, these protocols often take extended periods of time to complete, and may lead to a damaged gas sensor if not followed correctly. For example, upon installing the barrier using a threaded method, damage to a sealing mechanism may occur during installation.

Contrary to conventional systems, embodiments described herein provide a replaceable, ingress protection (IP) rated filter assembly that allows for an exclusive passage of gas to a gas sensor while protecting the gas sensor from moisture and debris. The Ingress Protection ratings, as defined in the international standard IEC 60529, classify the degree of protection provided against the intrusion of solid objects (including body parts), dust, accidental contact, and water in electrical enclosures. One example Ingress Protection rating is the IP66 rating which, per the standard, ensures complete protection against contact and dust, along with offering protection against moisture up to a specified degree which, per the standard, includes protection against water from powerful jets such that water does not enter the enclosure in harmful quantities. Additionally, while protecting the gas sensor from moisture and debris per an ingress protection standard, the filter assembly allows the gas sensor to remain compliant with regulatory time response standards (T20, T50, T90) for gas sensing. The design of the filter assembly also meets these standard response times without the use of a software accelerator.

In addition, since at least some process installations may involve highly volatile or even explosive environments, it is often beneficial, or even required, for devices that operate in such environments to comply with intrinsic safety requirements. These requirements help ensure that compliant electrical devices will not generate a source of ignition even under fault conditions. One example of an Intrinsic Safety requirement is set forth in: APPROVAL STANDARD INTRINSICALLY SAFE APPARATUS AND ASSOCIATED APPARATUS FOR USE IN CLASS I, II and III, DIVISION NUMBER 1 HAZARDOUS (CLASSIFIED) LOCATIONS, CLASS NUMBER 3610, promulgated by Factory Mutual Research October, 1998.

Figure 1:
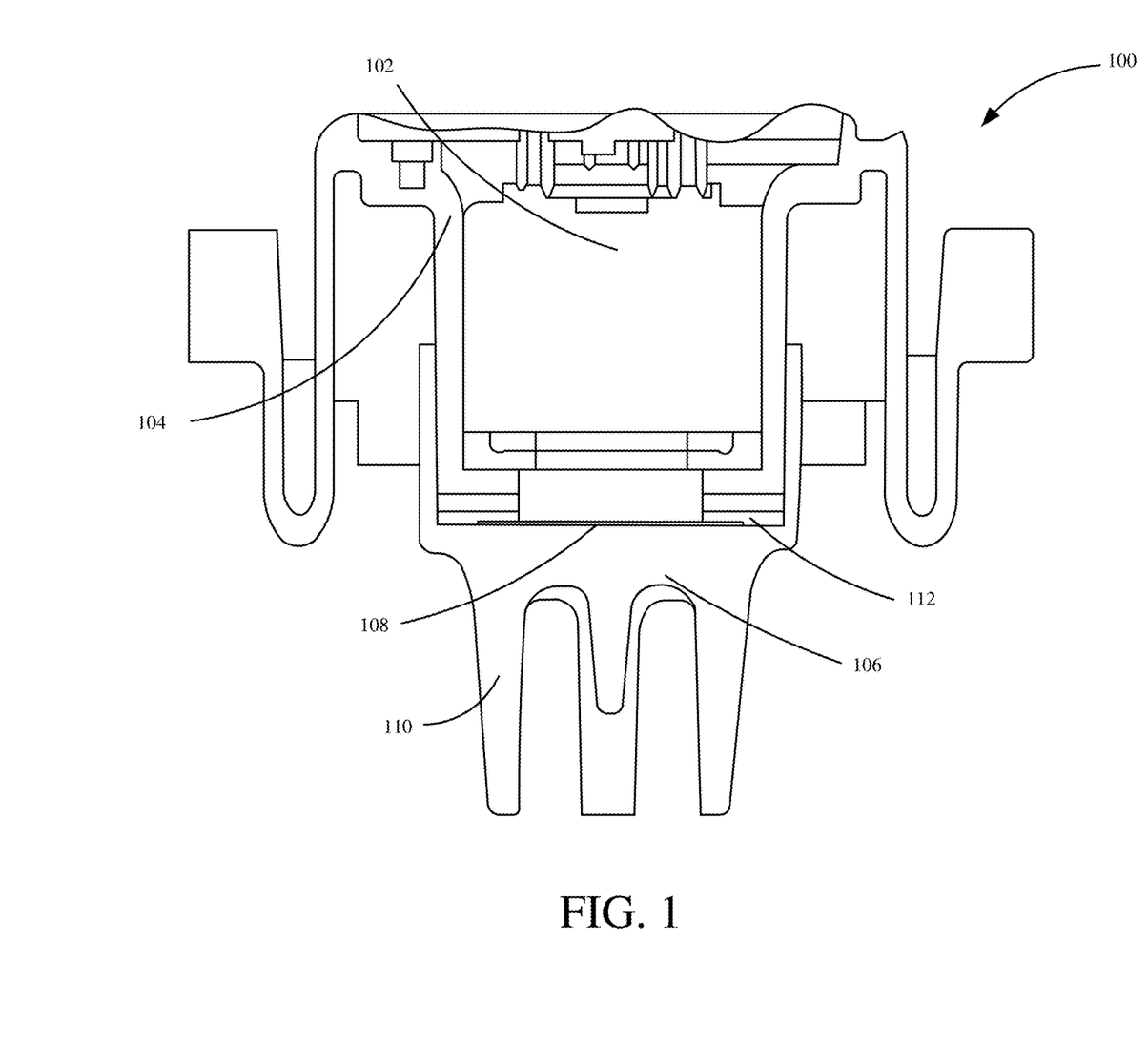
FIG. 1 is a cross sectional view of a gas sensor module coupled to a filter assembly in accordance with an embodiment of the present invention.

FIG. 1 shows a cross sectional view of a gas sensor module coupled to a filter assembly in accordance with an embodiment of the present invention. Gas detection device 100 includes a gas sensor module (e.g., generally a gas sensor 102 within a gas sensor housing 104) coupled to a filter assembly 106. Gas sensor 102 may be configured to detect combustible, toxic, and/or flammable gases present in a particular environment. Filter assembly 106, in one embodiment, is configured to protect gas sensor 102 from debris and moisture while still allowing gas sensor 102 to provide accurate readings in accordance with industry standard response times.

Filter assembly 106, in one embodiment, includes a filter housing 110. In one embodiment, upon coupling filter assembly 106 and gas sensor housing 104, filter housing 110 is configured to encircle a lower portion of gas sensor housing 104. Filter housing 110 may include any suitable design that allows gas sensor 102 to provide and maintain accurate readings in accordance with industry standards, while allowing for a protection against debris and moisture.

Filter assembly 106 may also include a gasket 112 and a filter element 108, each configured to be compressed against gas sensor housing 104 upon coupling filter assembly 106 to gas sensor housing 104. In one embodiment, filter element 108 is disposed at or near the center of filter assembly 106, and at least a portion of gasket 112 is placed on top of filter element 108. Upon being compressed, gasket 112 and filter element 108, in one embodiment, create a compression seal and, along with filter housing 110, provide IP66 rated protection for gas sensor 102. Filter element 108 may include any permeable material configured to allow for an exclusive passage of gas, thereby allowing gas sensor 102 to provide accurate readings in accordance with industry standard response times. In addition, filter element 108 may also include a hydrophobic, permeable material configured to allow for an exclusive passage of gas while inhibiting moisture from reaching gas sensor 102. Gasket 112 may include a hydrophobic material configured to inhibit moisture from reaching gas sensor 102.

Figure 2:
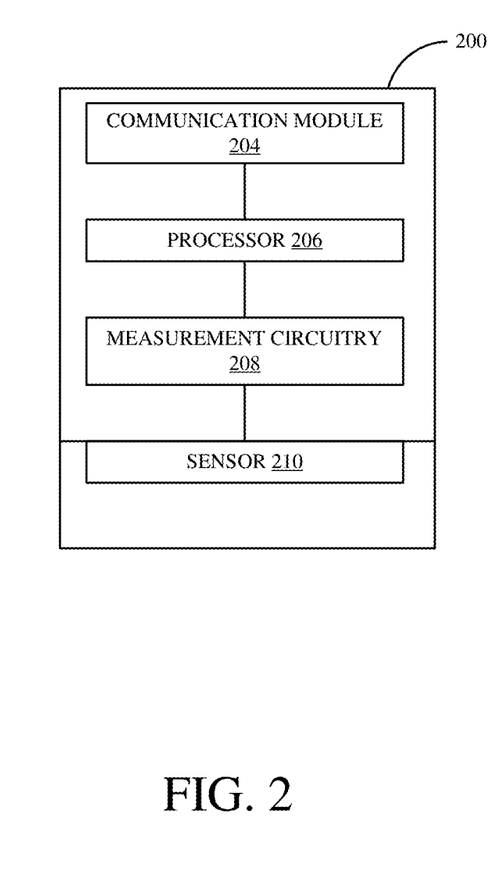
FIG. 2 is a block diagram of a gas sensor module in accordance with an embodiment of the present invention.

FIG. 2 is a diagrammatic system block diagram of a gas sensor module in accordance with an embodiment of the present invention. It is preferred that gas sensor module 200 comply with at least one intrinsic safety specification, such as that listed above, in order to help ensure safety in potentially explosive environments. Gas sensor module 200 includes a communication module 204 that is couplable to transmitter or other suitable device for conveying gas detection information to a control system, annunciation panel, or any other suitable device. This communication is in accordance with any suitable protocol. Communication module 204 is coupled to processor 206, which may be, in some embodiments, a microprocessor. Processor 206 is coupled to measurement circuitry 208 and is able to programmatically calculate one or more process variables, indicative of a gas, based on measurements of the raw sensor values obtained from measurement circuitry 208. Measurement circuitry 208, in one embodiment, is configured to receive signal information generated by sensor 210 and may include one or more suitable analog-to-digital converters as well as linearization circuitry and/or suitable filters, as appropriate.

Figure 3:
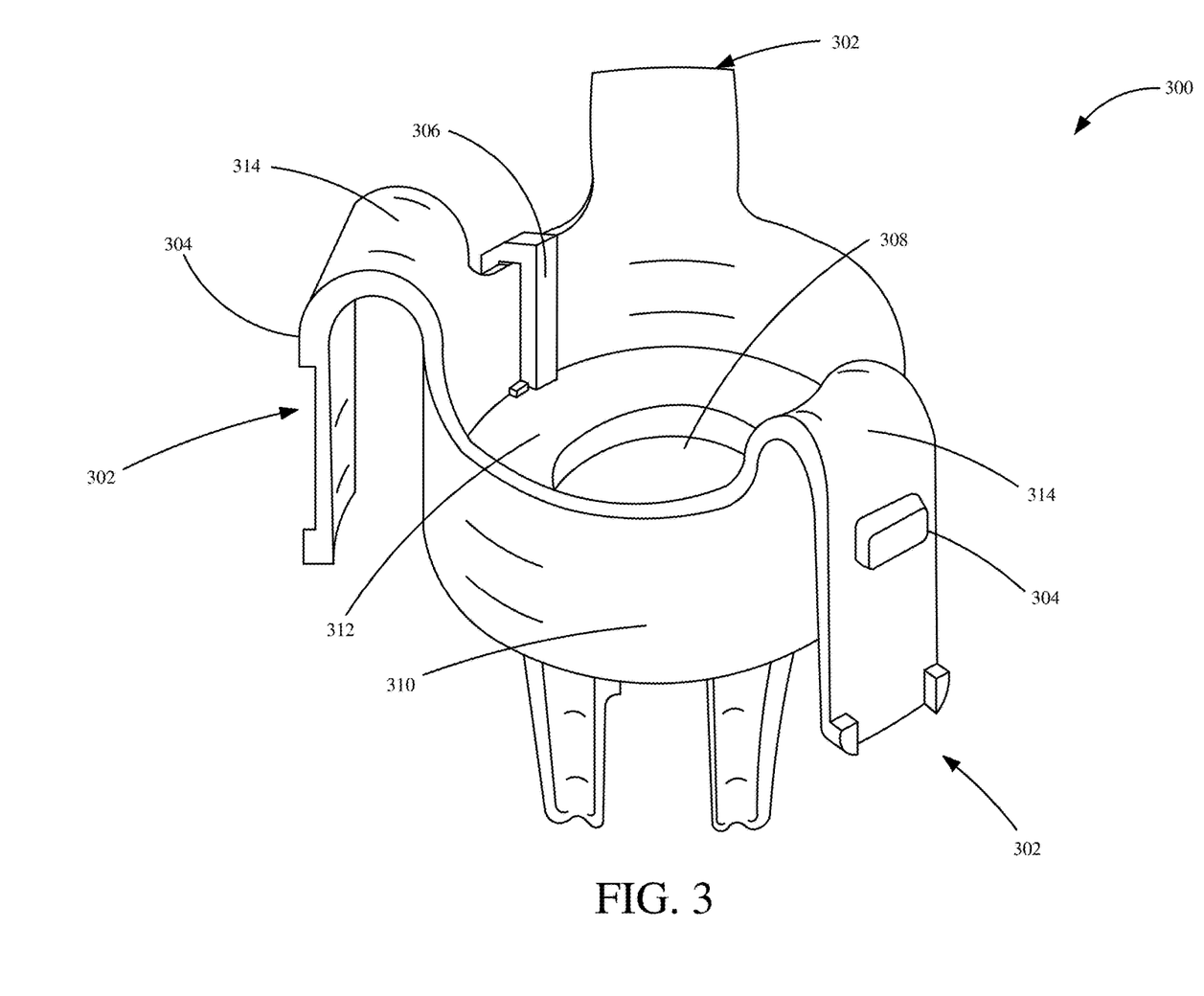
FIG. 3 is a diagrammatic view of a filter assembly that is field-replaceable in accordance with an embodiment of the present invention.

FIG. 3 is a diagrammatic view of a filter assembly that is field-replaceable in accordance with an embodiment of the present invention. Filter assembly 300, in one embodiment, is configured to protect a gas sensor (e.g. gas sensor 102 shown in FIG. 1) from moisture and debris in accordance with an Ingress Protection standard. In one embodiment, filter assembly 300 is configured to allow for an exclusive passage of gas, from an exterior environment, to a gas sensor, while inhibiting passage of moisture and/or debris. In one embodiment, filter assembly 300 is configured to be tool-lessly coupled to a gas sensor housing (e.g. gas sensor housing 104 shown in FIG. 1). Filter assembly 300, in one embodiment, includes a filter housing 310 with latching features 302 configured to couple filter assembly 300 to a gas sensor housing. In addition, filter housing 310 may include an alignment mechanism 306 configured to align filter assembly 300 with a gas sensor housing prior to the coupling of filter assembly 300 to the gas sensor housing.

Filter assembly 300 may include a filter element 308, disposed at or near the center of filter assembly 300. Filter assembly 300 may also include a gasket 312, such that at least a portion of gasket 312 is placed on top of filter element 308. In one embodiment, filter element 308 includes a permeable material configured to allow for a passage of gas. In one embodiment, filter element 308 includes a hydrophobic, permeable material. In one embodiment, upon coupling filter assembly 300 to a gas sensor housing using latching features 302, filter element 308 and gasket 312 become compressed, creating a seal between filter housing 310 and the gas sensor housing. In one embodiment, this compression provides an IP66 rated seal, as long as filter assembly 300 is coupled to the gas sensor housing, while still allowing a gas sensor to be responsive in accordance with known industry standards.

In one embodiment, latching features 302 may include an inverted "U" shaped body 314 and a protrusion 304. Protrusion 304, in one embodiment, is configured to be received by a receiving portion in a gas sensor housing, and, upon being received, couple filter assembly 300 to a gas sensor housing. As illustratively shown, filter assembly 300 includes three latching features generally represented by reference numeral 302, however, in other embodiments, it is expressly contemplated that any suitable number of latching features may be used in accordance with an embodiment of the present invention.

In one embodiment, latching features 302 allow for a tool-less coupling of filter assembly 300 and a gas sensor housing. For example, but not by limitation, upon applying an insertion force, latching features 302 may latch to a receiving portion on a gas sensor housing, therein securing filter assembly 300 to the gas sensor housing without requiring any tools. In one embodiment, filter assembly 300 may then be removed by hand from the gas sensor housing by compressing latching features 302 and pulling filter assembly 300 from the gas sensor housing.

Prior to the coupling of filter assembly 300 to a gas sensor housing using one or more latching features 302, alignment mechanism 306 may orient filter assembly 300 such that the one or more latching features 302 are in a proper orientation to the gas sensor housing. This, in one embodiment, ensures that filter assembly 300 may be installed without risk of damage to the gas sensor and/or the gas sensor housing. In one embodiment, alignment mechanism 306 includes a groove within a sidewall of filter housing 310, and is configured to align with, and axially receive, a corresponding alignment portion on a gas sensor housing. In one embodiment, the alignment between alignment mechanism 306 and a corresponding alignment portion ensures that filter assembly 300 is coupled to a gas sensor housing when in a proper rotational orientation. A proper rotational orientation, in one embodiment, is when the gas sensor housing and filter assembly 300 are properly oriented, with respect to one another. In one embodiment, the corresponding alignment portion may include an axial ridge configured to be axially received by alignment mechanism 306. However, in other embodiments, alignment mechanism 306 may include any other distinguishing mark, groove, or protrusion that is configured to align with a corresponding alignment portion on a gas sensor housing.

In other embodiments, a particular alignment mechanism 306 may be unique to a particular type of filter assembly 300. For example, but not by limitation, this may include a filter assembly 300 having a unique alignment mechanism indicating that filter assembly 300 is configured to be used with a particular type of gas sensor. For example, but not by limitation, filter assembly 300 may have a unique alignment mechanism 306 indicating that filter assembly 300 is configured to be used with a hydrocarbon gas sensor, or that filter assembly 300 is configured to be used with a non-hydrocarbon gas sensor. In one embodiment, this ensures that filter assembly 300 is only used with an appropriate, corresponding gas sensor.

Figure 4A:
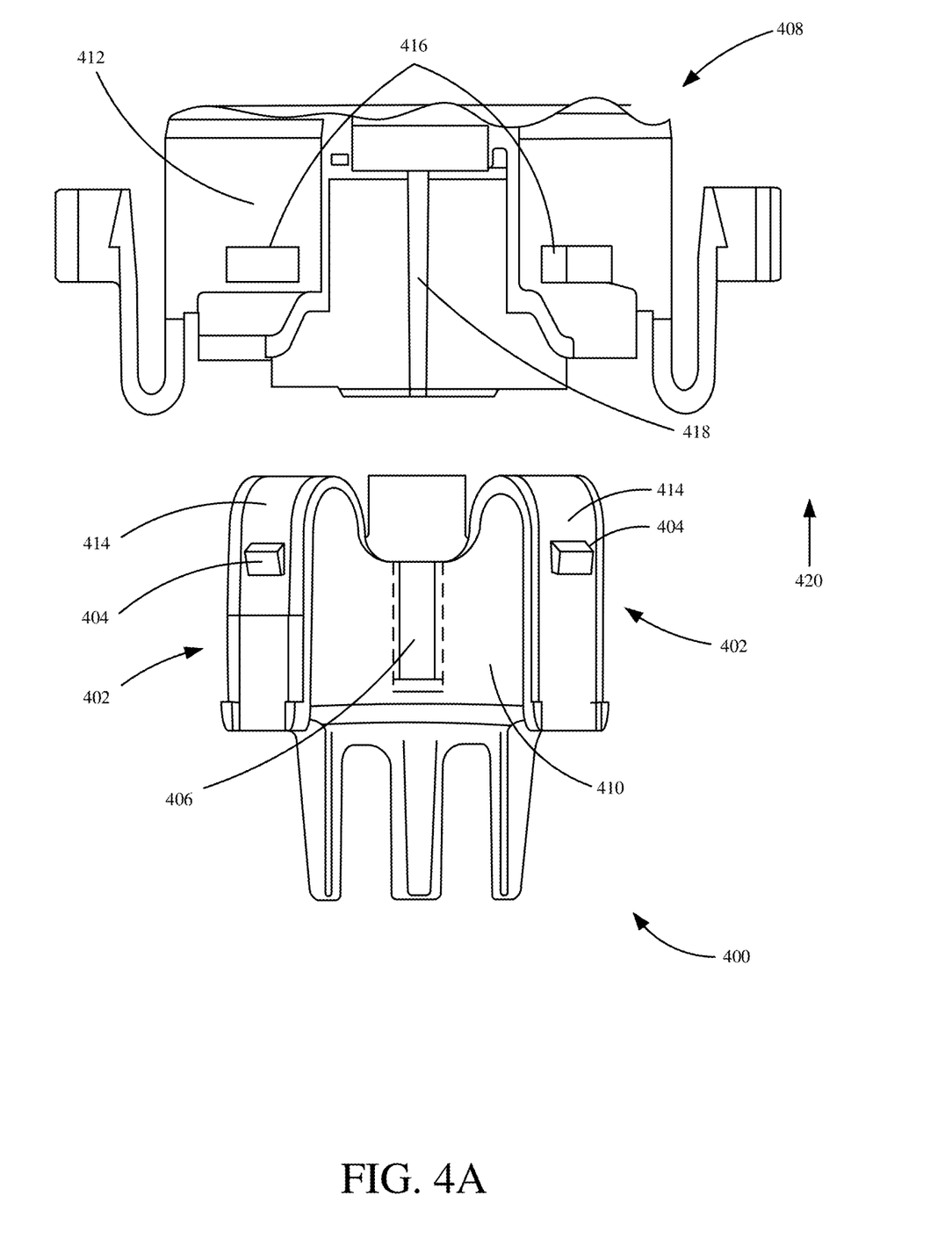
FIGS. 4A and 4B are diagrammatic views of a filter assembly aligned with a gas sensor module in accordance with an embodiment of the present invention.
Figure 4B:
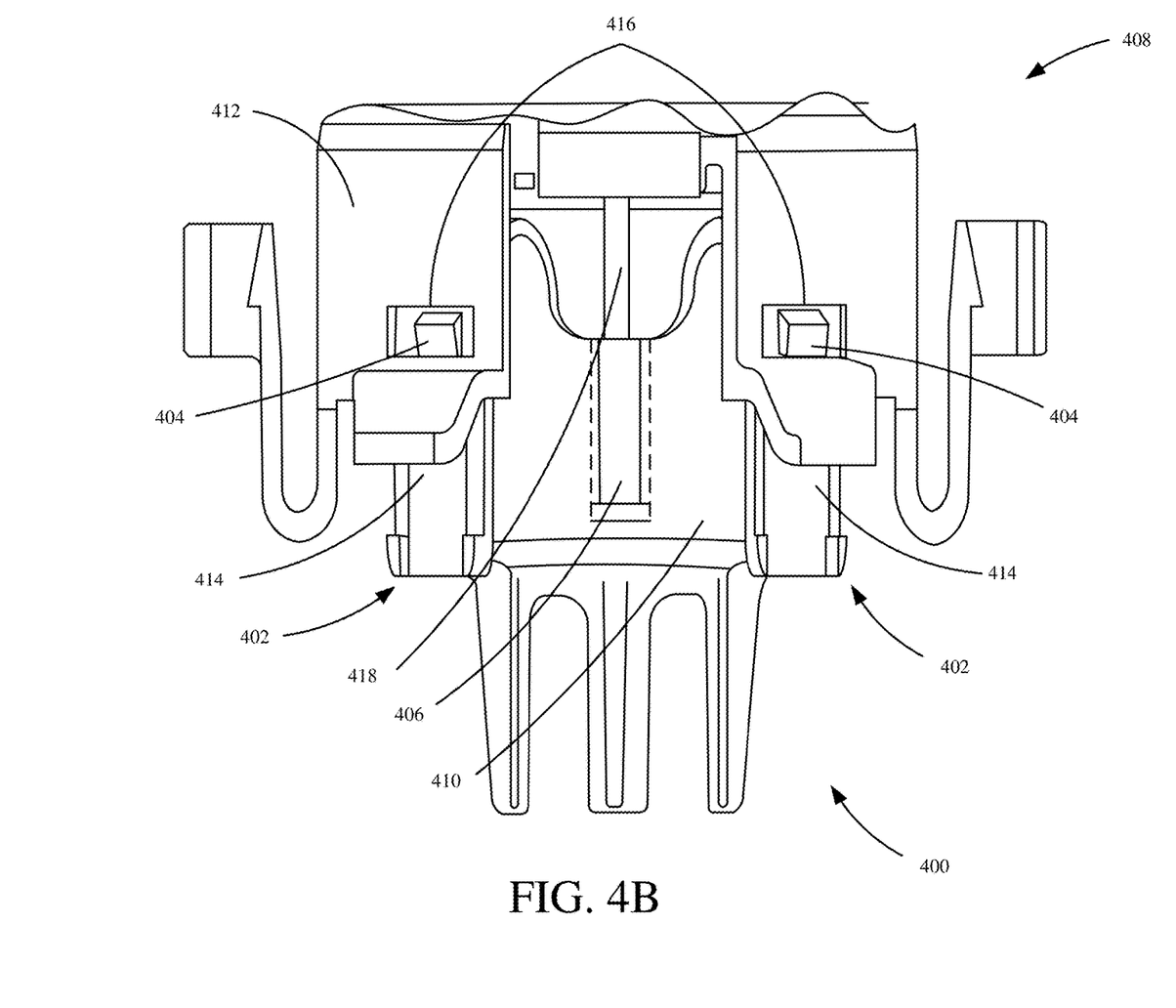

FIGS. 4A and 4B are diagrammatic views of a filter assembly aligned with a gas sensor module in accordance with an embodiment of the present invention.

FIG. 4A illustrates a filter assembly 400 aligned with a gas sensor module 408. In one embodiment, gas sensor module 408 includes a gas sensor (not shown) within a gas sensor housing 412. In one embodiment, filter assembly 400 is coupled to gas sensor housing 412 using a straight-line insertion operation, as illustratively shown in FIGS. 4A and 4B, such that any potential damage to the gas sensor or gas sensor housing 412 which (typically occurs in conventional, threaded designs) is mitigated. The straight-line insertion operation, in one embodiment, includes aligning an alignment mechanism 406 of a filter housing 410 with a corresponding alignment portion 418 on gas sensor housing 412, and applying an insertion force in a direction generally indicated by arrow 420, such that latching features 402 of filter assembly 400 latch to receiving portions 416. For example, FIG. 4A shows aligning alignment mechanism 406 with corresponding alignment portion 418, and FIG. 4B shows filter assembly 400 coupled to gas sensor housing 412 after an insertion force is applied. As used herein, a straight-line insertion operation is intended to mean that the two components do not rotate relative to one another during the operation. This is advantageous as it prevents rotation that could damage the compression seal.

In one embodiment, latching features 402 include an inverted "U" shaped body 414 with a protrusion 404. Protrusions 404, in one embodiment, are configured to be received by receiving portions 416, respectively, of gas sensor module 408 upon applying an insertion force in the direction generally indicated by arrow 420. In one embodiment, alignment mechanism 406 is a groove configured to come into contact with corresponding alignment portion 418. In one embodiment, corresponding alignment portion 418 includes an axial ridge. In one embodiment, filter assembly 400 is tool-lessly coupled to gas sensor housing 412 using the straight-line insertion operation.

FIG. 4B illustrates a gas detection device after insertion force 420 is applied to filter assembly 400, such that filter assembly 400 is coupled to gas sensor module 408. As illustratively shown, protrusions 404, of latching features 402, are received by receiving portions 416, respectively, of gas sensor housing 412. Additionally, corresponding alignment portion 418, of gas sensor module 408, is received by alignment mechanism 406 of filter assembly 400. In one embodiment, filter assembly 400 may be removed from gas sensor module 408 by hand, without the use of tools, through the compression of latching features 402 and subsequent pulling of filter assembly 400 from gas sensor module 408.

Figure 5:
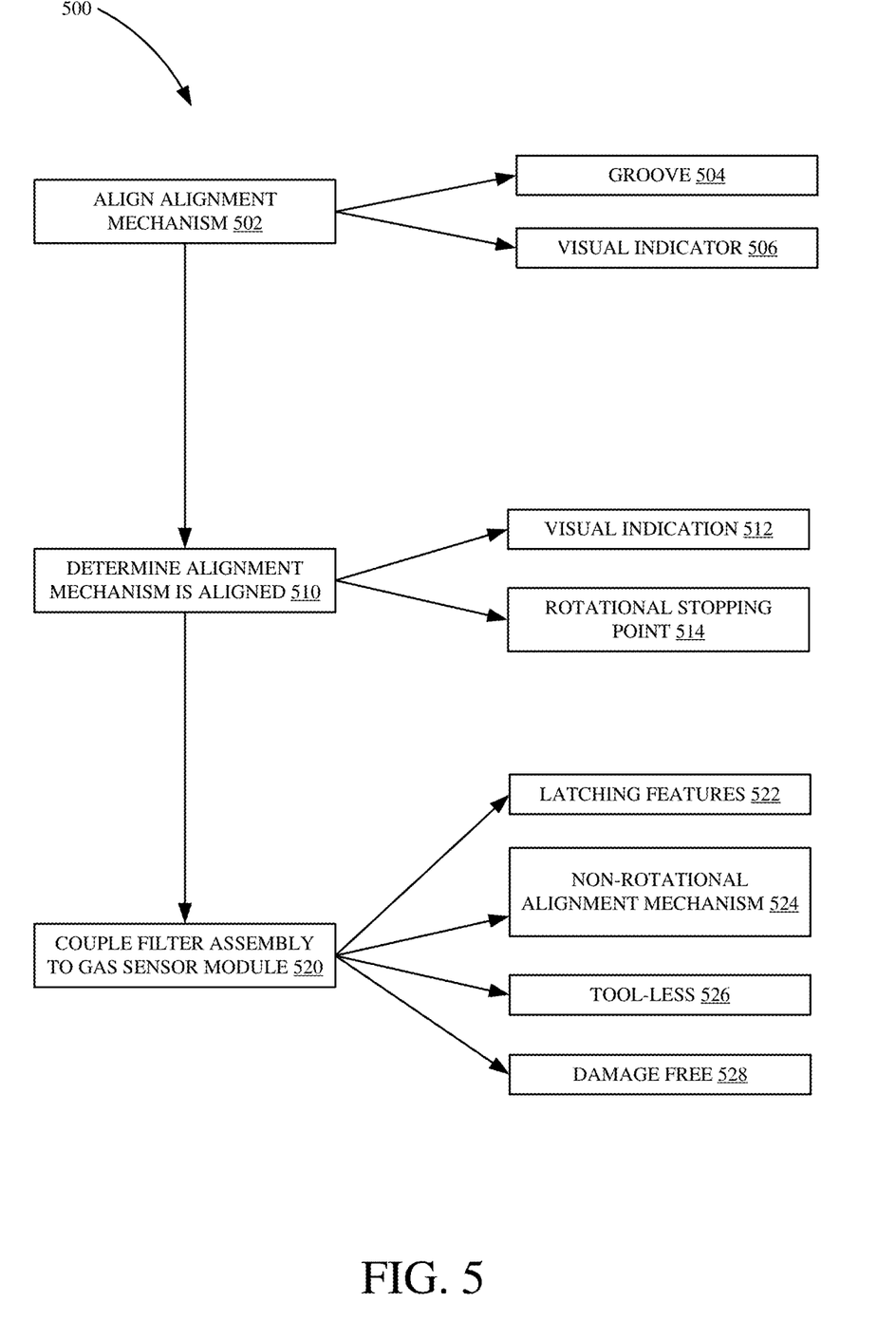
FIG. 5 is a flow diagram illustrating an operation of coupling a filter assembly to a gas sensor module in accordance with an embodiment of the present invention.

FIG. 5 is a flow diagram of installing a filter assembly to a gas sensor module in accordance with an embodiment of the present invention. Method 500 may be useful in installing a filter assembly without needing tools or having to thread a portion of a filter which may lead to damage of a gas sensor module. Method 500 begins at block 502, where a user aligns an alignment mechanism of a filter assembly with a corresponding alignment portion on a gas sensor module. While method 500 may be performed by a user, it is also expressly contemplated that in other embodiments, method 500 is performed automatically during manufacture. In one embodiment, the alignment mechanism includes a groove, as indicated at block 504, configured to receive the corresponding alignment portion on the gas sensor module. In one embodiment, the groove is specific to the corresponding alignment portion, such that the filter assembly is only coupled to the gas sensor module after aligning the alignment mechanism with the corresponding alignment portion. In one embodiment, this ensures that the filter assembly is in a correct rotational orientation prior to applying an insertion force. In one embodiment, the alignment mechanism includes a visual indicator, as indicated at block 506. In one embodiment, the visual indicator may include a color or a pattern on the filter assembly.

At block 510, a user determines that an alignment mechanism of a filter assembly is aligned with a corresponding alignment portion on a gas sensor module. In one embodiment, a determination may include a visual indication, as indicated at block 512. The visual indication may include an actuated light or a pattern that forms when the alignment mechanism is aligned with the corresponding alignment portion on the gas sensor module, for example. In another embodiment, a determination may include a rotational stopping point, as indicated at block 514. As the filter assembly is rotated relative to the gas sensor module, the rotational stopping point may cease rotational movement of the filter assembly once the alignment mechanism and the corresponding alignment portion are aligned. In addition, other detection mechanisms are envisioned in other embodiments.

At block 520, a user applies an insertion force to a filter assembly such that the filter assembly becomes coupled to a gas sensor module. In one embodiment, the insertion force is applied to the filter assembly until latching features of the filter assembly latch to a gas sensor housing of the gas sensor module, as indicated at block 522. In one embodiment, the filter assembly is securely fastened to the gas sensor module upon a mechanical latching of latching features to the gas sensor housing. In another embodiment, as the filter assembly is coupled to the gas sensor module, an alignment mechanism of the filter assembly receives a corresponding alignment portion of the gas sensor module, as indicated at block 524. In one embodiment, the insertion of the filter assembly into the gas sensor module is done without any tools, as indicated at block 526. In one embodiment, the insertion of the filter assembly into the gas sensor module in accordance with methods discussed herein, ensures that there is no damage done to the gas sensor, as indicated at block 528.

Thus, method 500 allows a user to install a filter assembly without having to follow a particular protocol requiring significant amounts of time or a variety of tools.

Although the present invention has been described with reference to preferred embodiments, workers skilled in the art will recognize that changes may be made in form and detail without departing from the spirit and scope of the invention.

What is claimed is:

1. A gas detection device comprising:
   a gas sensor module configured to detect a gas, the gas sensor module including;
      a gas sensor disposed within a gas sensor housing;
      circuitry coupled to the gas sensor housing, the circuitry being configured to provide an indication of the gas;
   a filter assembly configured to sealingly couple to the gas sensor housing via a straight line insertion operation and protect the gas sensor from particulates; and
   wherein the tilter assembly comprises an alignment mechanism configured to align with a corresponding alignment portion on the gas sensor housing such that the filter assembly may only be coupled to the sensor housing in a single rotational orientation.

2. The gas detection device of claim 1, wherein the alignment mechanism is a groove on the filter assembly configured to receive the corresponding alignment portion on the gas sensor housing.

3. The gas detection device of claim 1, wherein the filter assembly is configured to be tool-lessly coupled to the gas sensor housing.

4. The gas detection device of claim 1, wherein the gas detection device is intrinsically-safe.

5. The gas detection device of claim 1, wherein the filter assembly further comprises at least one latching feature configured to couple to the gas sensor housing.

6. The gas detection device of claim 1, wherein the gas sensor has a type, and wherein the filter assembly has an alignment mechanism that corresponds to the gas sensor type.

7. The gas detection device of claim 1, wherein the filter assembly is removable from the gas sensor housing without using any tools.

8. The gas detection device of claim 1, wherein the filter assembly comprises a filter element permeable to the gas.

9. The gas detection device of claim 1, wherein the filter assembly further comprises a gasket and a filter element configured to create a compression seal upon coupling the filter assembly to the gas sensor housing and allow for an exclusive passage of the gas.

10. The gas detection device of claim 9, wherein the filter element is hydrophobic.

11. The gas detection device of claim 9, wherein the compression seal is an ingress-protection rated seal.

\* \* \* \* \*

UNITED STATES PATENT AND TRADEMARK OFFICE
CERTIFICATE OF CORRECTION

| | | |
|---|---|---|
| PATENT NO. | : 10,617,985 B2 | Page 1 of 1 |
| APPLICATION NO. | : 15/449359 | |
| DATED | : April 14, 2020 | |
| INVENTOR(S) | : Mark B. Morris, Greg E. Gindele and Hun Chhuoy | |

It is certified that error appears in the above-identified patent and that said Letters Patent is hereby corrected as shown below:

On the Title Page

Page 2, Other Publications, Line 13, delete "2419112452" and insert --2019112452--

In the Claims

Column 6, Line 51, Claim 1, delete "tilter" and insert --filter--

Signed and Sealed this
Twenty-fifth Day of October, 2022

Katherine Kelly Vidal
*Director of the United States Patent and Trademark Office*